US012714883B2

(12) United States Patent
Honda et al.

(10) Patent No.: US 12,714,883 B2
(45) Date of Patent: Aug. 25, 2026

(54) IRRADIATION NOZZLE, PARTICLE THERAPY APPARATUS, PARTICLE THERAPY SYSTEM, AND METHOD FOR CONTROLLING PARTICLE THERAPY SYSTEM

(71) Applicant: Hitachi High-Tech Corporation, Tokyo (JP)

(72) Inventors: Taizo Honda, Tokyo (JP); Chihiro Nakashima, Tokyo (JP); Tomokazu Shimakura, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 526 days.

(21) Appl. No.: 18/279,427

(22) PCT Filed: Feb. 15, 2022

(86) PCT No.: PCT/JP2022/005843
§ 371 (c)(1),
(2) Date: Aug. 30, 2023

(87) PCT Pub. No.: WO2022/185898
PCT Pub. Date: Sep. 9, 2022

(65) Prior Publication Data

US 2024/0189625 A1 Jun. 13, 2024

(30) Foreign Application Priority Data

Mar. 5, 2021 (JP) ................................ 2021-035540

(51) Int. Cl.
*A61N 5/10* (2006.01)

(52) U.S. Cl.
CPC ......... *A61N 5/1081* (2013.01); *A61N 5/1078* (2013.01)

(58) Field of Classification Search
CPC ................ A61N 5/1081; A61N 5/1078; A61N 2005/1061; A61N 2005/1087
See application file for complete search history.

(56) References Cited

U.S. PATENT DOCUMENTS

2004/0037390 A1* 2/2004 Mihara ................ A61N 5/1049 378/65
2007/0131876 A1 6/2007 Brahme
(Continued)

FOREIGN PATENT DOCUMENTS

EP 3 251 600 A1 12/2017
JP 2016-129639 A 7/2016
(Continued)

OTHER PUBLICATIONS

Japanese Office Action received in corresponding Japanese Application No. 2021-035540 dated Mar. 12, 2024.
(Continued)

*Primary Examiner* — Bo Joseph Peng
(74) *Attorney, Agent, or Firm* — MATTINGLY & MALUR, PC

(57) ABSTRACT

To implement downsizing of an apparatus and highly accurate beam irradiation. An irradiation nozzle 4 that irradiates a target object Pt with a radiotherapy beam includes: a nozzle base part 42 fixed on a beam axis 40 through which the radiotherapy beam passes; and a nozzle tip part that irradiates the target object with the radiotherapy beam that has passed through the nozzle base part, in which the nozzle tip part is fixed at a first position when the target object is irradiated with the radiotherapy beam and is fixed at a second position when the target object is imaged, and a curved movement path in which the nozzle tip part is movable between the first position and the second position is provided.

17 Claims, 12 Drawing Sheets

(56) References Cited

U.S. PATENT DOCUMENTS

| | | | | |
|---|---|---|---|---|
| 2013/0066134 | A1 | 3/2013 | Carol | |
| 2014/0321615 | A1* | 10/2014 | Carlsson | A61N 5/1049 378/62 |
| 2016/0074673 | A1* | 3/2016 | Allen | A61N 5/1049 600/1 |
| 2017/0203125 | A1 | 7/2017 | Amato et al. | |
| 2017/0340903 | A1* | 11/2017 | Ie | A61B 6/4452 |
| 2018/0064955 | A1 | 3/2018 | Iseki | |
| 2019/0168025 | A1 | 6/2019 | Koponen et al. | |
| 2021/0370094 | A1* | 12/2021 | Honda | A61N 5/01 |
| 2024/0189625 | A1* | 6/2024 | Honda | A61N 5/1078 |

FOREIGN PATENT DOCUMENTS

| | | | |
|---|---|---|---|
| JP | 2020-130863 | A | 8/2020 |
| KR | 10-2019-0064541 | A | 6/2019 |
| WO | 2021/009281 | A1 | 1/2021 |

OTHER PUBLICATIONS

Extended European Search Report received in corresponding European Application No. 22762955.7 dated Dec. 13, 2024.
International Search Report of PCT/JP2022/005843 dated Apr. 12, 2022.

* cited by examiner

IRRADIATION NOZZLE, PARTICLE THERAPY APPARATUS, PARTICLE THERAPY SYSTEM, AND METHOD FOR CONTROLLING PARTICLE THERAPY SYSTEM

TECHNICAL FIELD

The present invention relates to an irradiation nozzle, a particle therapy apparatus, a particle therapy system, and a method for controlling the particle therapy system.

BACKGROUND ART

An image guided radiation therapy (IGRT) enables more accurate irradiation of a target as compared to a radiotherapy according to the related art. In addition, a clinical target volume (CTV)-planning target volume (PTV) margin can be reduced, and a dose for a normal tissue can be reduced.

The accuracy of the IGRT is improved by matching isocenters of a radiotherapy apparatus and an imaging apparatus.

In order to implement the highly accurate IGRT in radiotherapy, it is necessary to obtain a high-quality diagnostic image (a diagnostic image with good contrast) at the isocenter.

The current computed tomography (CT) apparatuses can acquire high-quality images, but have large external dimensions. Therefore, in a case where an irradiation nozzle is disposed at a position where interference is avoided in order to capture an image at the isocenter, a distance from a nozzle tip to the isocenter becomes long.

As the distance from the nozzle tip to the isocenter increases, penumbrae at an edge of a radiation field increase, and thus the quality of dose distribution decreases. In particular, in particle therapy, a beam size increases, and controllability of the dose distribution deteriorates. Therefore, a technology for enabling a nozzle to move in a beam axis direction has been proposed (PTL 1).

CITATION LIST

Patent Literature

PTL 1: JP 2020-130863 A

SUMMARY OF INVENTION

Technical Problem

In the technology according to the related art described in PTL 1, since a retraction space on a beam axis is required for nozzle retraction, a treatment room becomes large and cost increases.

The present invention has been made in view of the above problems, and an object of the present invention is to provide an irradiation nozzle, a particle therapy apparatus, a particle therapy system, and a method for controlling the particle therapy system, which are capable of implementing downsizing of the apparatus and highly accurate beam irradiation.

Solution to Problem

In order to solve the above problem, an irradiation nozzle according to the present invention is an irradiation nozzle that irradiates a target object with a radiotherapy beam, the irradiation nozzle including: a nozzle base part fixed on a beam axis through which the radiotherapy beam passes; and a nozzle tip part that irradiates the target object with the radiotherapy beam that has passed through the nozzle base part, in which the nozzle tip part is fixed at a first position when the target object is irradiated with the radiotherapy beam and is fixed at a second position when the target object is imaged, and a curved movement path in which the nozzle tip part is movable between the first position and the second position is provided.

Advantageous Effects of Invention

According to the present invention, the target object can be irradiated with the radiotherapy beam when the nozzle tip part is fixed at the first position, and the target object can be imaged when the nozzle tip part is moved in a predetermined direction and fixed at the second position. Therefore, for example, the isocenter of the irradiation beam and the isocenter of the imaging can be matched, and the treatment and the imaging can be performed without moving a treatment target on a top plate, so that the treatment can be performed with high accuracy.

BRIEF DESCRIPTION OF DRAWINGS

FIG. 3 is a perspective view of the irradiation nozzle.

FIG. 4 is a side view of the irradiation nozzle when a nozzle tip part is at a retraction position.

FIG. 5 is a side view of the irradiation nozzle when the nozzle tip part is at an irradiation position.

DESCRIPTION OF EMBODIMENTS

Hereinafter, embodiments of the present invention will be described with reference to the drawings. When a nozzle tip part is at an irradiation position (first position) on a beam axis, an irradiation nozzle according to the present embodiment can irradiate a target object with a radiotherapy beam emitted from the nozzle tip part, the radiotherapy beam having passed through a nozzle base part. When irradiation with the radiotherapy beam is not performed, the nozzle tip part can be deviated from the beam axis while being moved toward an upstream side of the beam axis.

The radiotherapy beam is a particle beam. However, the present embodiment can be applied not only to a particle beam but also to an X-ray or an electron beam. Hereinafter, the radiotherapy beam may be simply referred to as a beam.

In the present embodiment, a CT apparatus will be described as an example of an imaging apparatus, but the imaging apparatus is not limited to the CT apparatus, and for example, another imaging apparatus such as a magnetic resonance imaging (MRI) apparatus, an X-ray imaging apparatus, or a positron emission tomography (PET) apparatus may be used.

Figure 1:
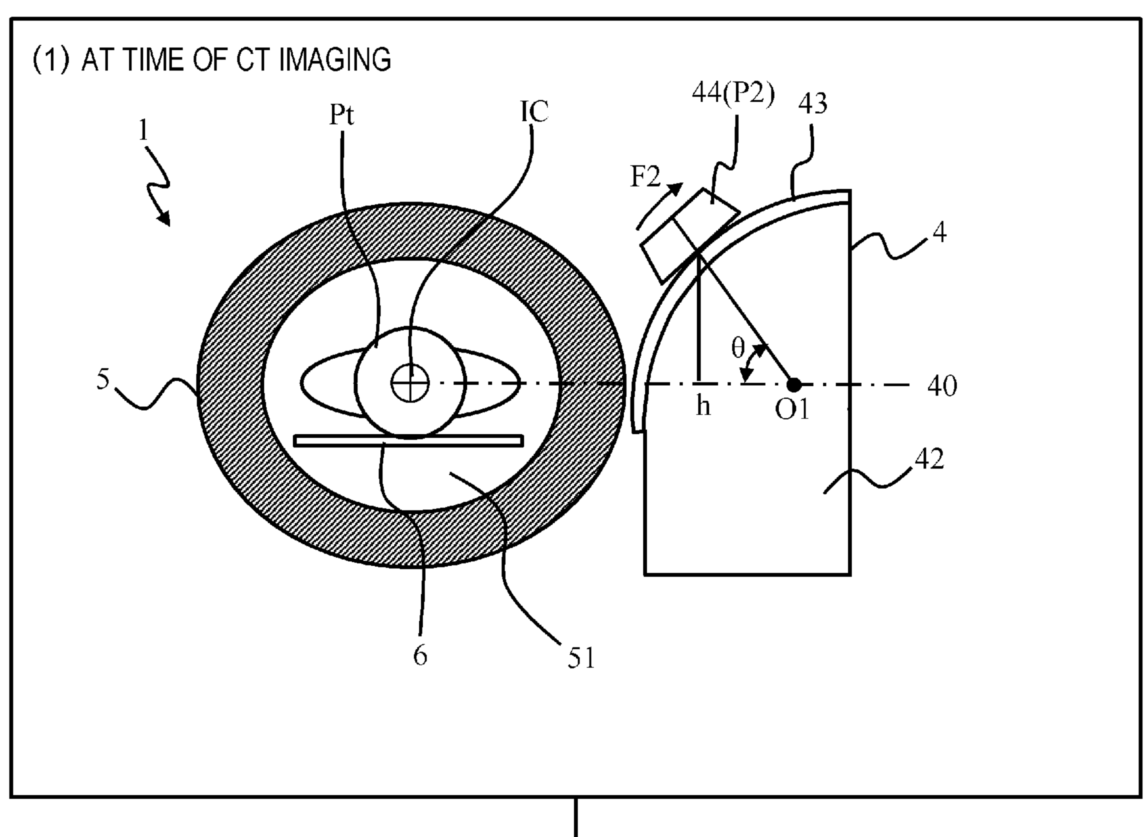
FIG. 1 is an explanatory view illustrating an overall outline of a particle therapy apparatus including an irradiation nozzle.
Figure 1:
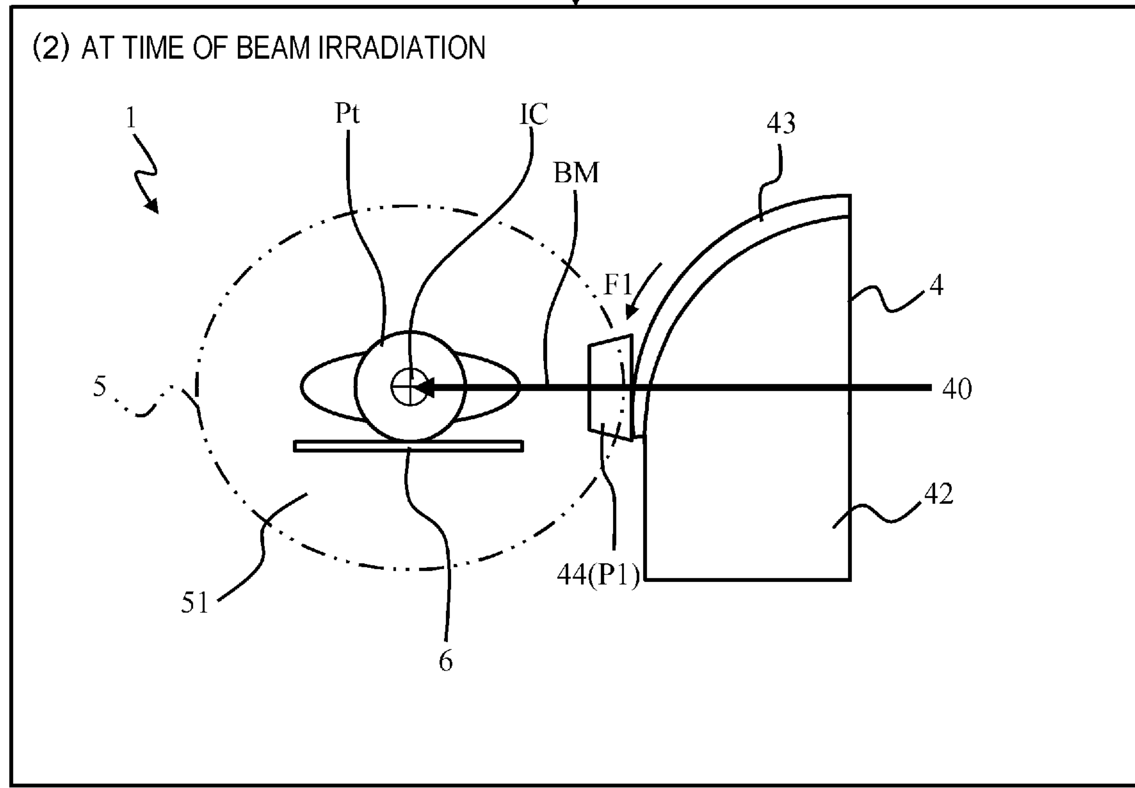

FIG. 1 is a view illustrating an overall outline of a particle therapy system 1 including an irradiation nozzle 4.

Figure 2:
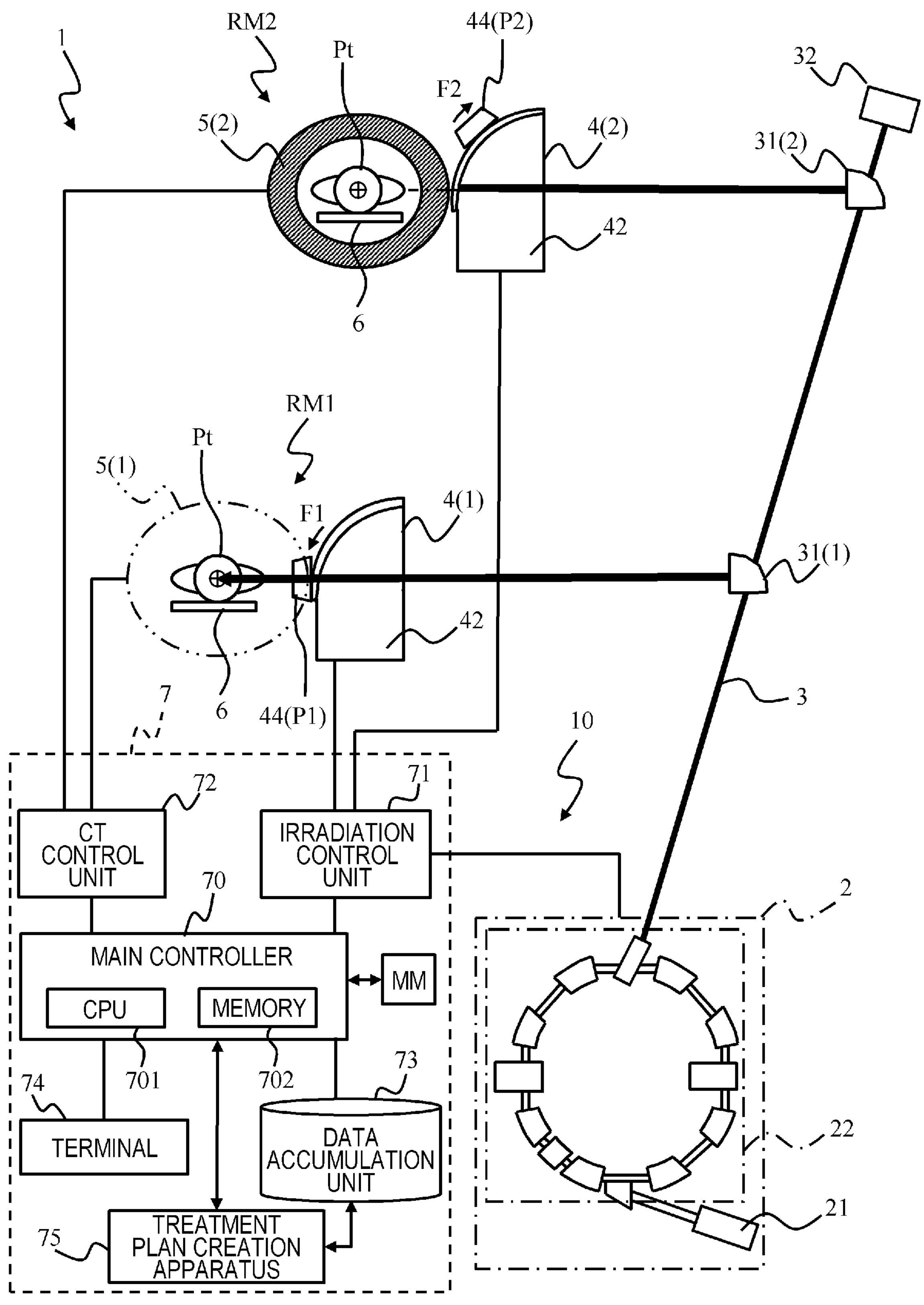
FIG. 2 is a configuration diagram of an entire system including the particle therapy apparatus.

A detailed configuration will be described below with reference to FIG. 2 and subsequent drawings. FIG. 1(1) illustrates imaging of a patient Pt by a CT apparatus 5. FIG. 1(2) illustrates irradiation of a target volume at an isocenter IC with a beam BM from the irradiation nozzle 4.

The irradiation nozzle 4 includes a nozzle base part 42 fixed to a beam axis 40 and a nozzle tip part 44 movable with respect to the nozzle base part 42 in predetermined directions F1 and F2. That is, the irradiation nozzle 4 of the present embodiment includes a fixed part (the nozzle base part 42) and a movable part (the nozzle tip part 44).

The beam BM from an accelerator 22 (to be described below with reference to FIG. 2) is injected to the nozzle base part 42 along the beam axis 40 from behind. A movement path 43 used when the nozzle tip part 44 moves is provided on a downstream side of the nozzle base part 42 on the beam axis. The downstream side on the beam axis refers to a downstream side in a beam flow direction, and corresponds to the substantially left side of the nozzle base part 42 in FIG. 1.

The nozzle tip part 44 moves between an irradiation position P1 where the isocenter IC is irradiated with the beam and a retraction position P2 by using the movement path 43. The nozzle tip part 44 moves on the movement path 43 by a nozzle drive unit 45 to be described below.

The nozzle tip part 44 being at the irradiation position P1, which is an example of a "first position", is indicated as the nozzle tip part 44 (P1) in the drawing. Similarly, the nozzle tip part 44 being at the retraction position P2, which is an example of a "second position", is indicated as the nozzle tip part 44 (P2) in the drawing.

The nozzle tip part 44 moves along the movement path 43 provided on a downstream side of the nozzle base part 42 on the beam axis.

The nozzle tip part 44 moves in a "predetermined direction" that is a direction in which an intersection h of a perpendicular line drawn from the nozzle tip part 44 to the beam axis 40 on the beam axis 40 approaches a point O1 (center point O1) positioned on a nozzle base part 42 side and set on the beam axis 40, on the arc-shaped movement path 43 connecting at least the irradiation position P1 and the retraction position P2 set above the center point O1 by a predetermined angle θ. The retraction position P2 is set at a position deviated from the beam axis 40.

As an example, the movement path 43 is formed in a curved shape connecting positions by rotating a predetermined angle of approximately 90 degrees clockwise from an intersection (the irradiation position P1) between the beam axis 40 and the downstream side of the nozzle base part 42 on the beam axis around the point O1 set on the beam axis 40 on the nozzle base part 42 side. The curved movement path 43 can also be referred to as the arc-shaped movement path 43. The arc shape is not limited to a part of a perfect circle, and may be a part of a circular shape other than the perfect circle. It is sufficient if the predetermined angle is an angle including an angle θ by which the nozzle tip part 44 moves between the irradiation position P1 and the retraction position P2, and may be 90 degrees or more or less than 90 degrees.

The irradiation nozzle 4 and the CT apparatus 5 are arranged in such a way as not to interfere with each other during operation of the main functions thereof, and the operation is controlled. The main function of the irradiation nozzle 4 is beam irradiation. The main function of the CT apparatus 5 is imaging.

Since the CT apparatus 5 stands by on a back side of the drawing at the time of beam irradiation by the irradiation nozzle 4, the CT apparatus 5 and the irradiation nozzle 4 do not come into contact with each other (FIG. 1(2)). At the time of imaging, the CT apparatus 5 moves from the standby position on the back side of the drawing to the front side of the drawing (FIG. 1(1)). Before the CT apparatus 5 moves from the standby position to the imaging position, the nozzle tip part 44 of the irradiation nozzle 4 moves to the retraction position P2, so that the CT apparatus 5 and the irradiation nozzle 4 do not come into contact with each other. The CT apparatus 5 may stand by on the front side of the drawing, or as will be described below with reference to FIG. 7, the CT apparatus 5 may be disposed in such a way as to be close to the nozzle tip part 44 (P1) when the nozzle tip part 44 is at the irradiation position P1. The CT apparatus 5 may be tiltable toward the irradiation nozzle 4.

The description will return to FIG. 1. At the time of imaging illustrated in FIG. 1(1), since the nozzle tip part 44 is at the retraction position P2, a protrusion (the nozzle tip part 44) does not exist on the downstream side of the nozzle base part 42 on the beam axis. Therefore, the CT apparatus 5 and the nozzle base part 42 can be brought close to each other by a thickness of the nozzle tip part 44.

At the time of irradiation illustrated in FIG. 1(2), the CT apparatus 5 returns to the standby position, and the nozzle tip part 44 moves from the retraction position P2 to the irradiation position P1. Here, it is not necessary to change a position of a couch 6 on which the patient Pt, who is a target object of beam irradiation, is placed when switching between the imaging by the CT apparatus 5 and the irradiation by the irradiation nozzle 4. In the particle therapy system of the present embodiment, since there is no change in position of the patient Pt (target volume) between the end of the imaging and the start of the irradiation, irradiation with the beam can be accurately performed according to information based on a captured image.

According to the present embodiment configured as described above, it is not necessary to move the patient Pt or change a posture between the CT imaging for positioning and the beam irradiation, and thus, it is possible to suppress fluctuation of a body tissue caused by the movement of the patient Pt or the like. Therefore, according to the present embodiment, since irradiation with the beam can be performed with highly accurate positioning, a margin for tissues around the target volume can be reduced, and a dose for a normal tissue can be reduced.

Furthermore, in the present embodiment, the nozzle tip part 44 of the irradiation nozzle 4 is moved away from the irradiation position P1 toward an upstream side on the beam axis 40 and moved in the direction F2 deviating from the beam axis 40 instead of being extended and contracted along the beam axis, so that the entire irradiation nozzle 4 can be downsized as compared with PTL 1.

First Embodiment

A first embodiment will be described with reference to FIGS. 2 to 8. FIG. 2 illustrates an overall configuration of the particle therapy system 1. The particle therapy system 1 includes, for example, at least a particle therapy apparatus 10 and the CT apparatus 5 which is an example of the "imaging apparatus". The particle therapy system 1 may further include an information processing system 7 as a "control apparatus" in addition to the particle therapy apparatus 10 and the CT apparatus 5.

The particle therapy system 1 can further include the couch 6 for holding the patient Pt at a predetermined position. The couch 6 can also be referred to as a "target object positioning control unit" that controls the position of the patient Pt who is a target object. The couch 6 can move the patient Pt in a plurality of directions by a movement mechanism such as an arm robot (not illustrated). In addition, a bed on which the patient Pt lies on a top plate will be described as an example of the couch 6, but a chair type couch on which the patient Pt sits may also be used, and the chair type couch 6 may be movable or fixed. In addition, the type of the couch 6 may be a type in which the patient Pt receives treatment in an upright position.

The particle therapy apparatus 10 includes, for example, the irradiation nozzle 4 and the accelerator 2. The particle therapy apparatus 10 may further include a component other than the irradiation nozzle 4 and the accelerator 2.

The configuration of the particle therapy system 1 will be described with reference to FIG. 2. A particle generator 2 includes, for example, an ion source (not illustrated), a linear accelerator 21 as a pre accelerator, and a synchrotron accelerator 22. Instead of a configuration using the pre accelerator 20 and the synchrotron 21, for example, a cyclotron or a synchrocyclotron may be used, or a particle accelerator using a superconducting magnet may be used. Examples of the particle beam include a proton beam (proton ion beam), a helium beam (helium ion beam), and a carbon beam (carbon ion beam). Any one of them may be used.

The accelerator 22 includes, for example, an annular beam duct, an injector, a plurality of bending magnets, a plurality of quadrupole magnets, a radio frequency acceleration cavity, a radiofrequency acceleration system for extraction, and a septum magnet for extraction (all reference signs are omitted).

A beam generated by the particle generator 2 is supplied to each of irradiation nozzles 4 (1) and 4 (2) in irradiation rooms RM1 and RM2 by the beam transport system 3. Although two irradiation rooms RM1 and RM2 are illustrated in FIG. 2, the number of irradiation rooms is not limited. The particle therapy system 1 of the present embodiment can support one irradiation room or three or more irradiation rooms.

The beam from the beam transport system 3 is injected to the irradiation nozzle 4 (1) in the treatment room RM1 by a bending magnet 31 (1). Similarly, the beam from the beam transport system 3 is injected to the irradiation nozzle 4 (2) in the treatment room RM2 by a bending magnet 31 (2).

In the first treatment room RM1, the nozzle tip part 44 (P1) at the irradiation position P1 irradiates the isocenter IC with the beam. In the second treatment room RM2, the nozzle tip part 44 (P2) is at the retraction position P2, and the CT apparatus 5 moves to the imaging position to image the periphery of the target volume of the patient Pt. A detailed configuration of the irradiation nozzle 4 will be described below with reference to FIGS. 3 to 5. In a case where the treatment rooms RM1 and RM2 need not be distinguished, the treatment rooms RM1 and RM2 are referred to as the treatment room RM.

The information processing system 7 controls the particle therapy system 1. The information processing system 7 includes, for example, a main controller 70, an irradiation control unit 71, a CT control unit 72, a data accumulation unit 73, an operation terminal 74, and a treatment plan creation apparatus 75.

The main controller 70 is a computer that controls the entire operation of the particle therapy system 1, and includes computer resources such as a microprocessor 701 and a memory 702. In the drawing, the microprocessor 701 is indicated as a "central processing unit (CPU)". The memory 702 stores a predetermined computer program (not illustrated) used to control the particle therapy system 1.

The microprocessor 701 controls the particle therapy system 1 by reading and executing the predetermined computer program from the memory 702. The main controller 70 communicates with the irradiation control unit 71, the CT control unit 72, the data accumulation unit 73, the operation terminal 74, and the treatment plan creation apparatus 75 via a communication interface unit (not illustrated) or the like.

A storage medium MM can be connected to the main controller 70. Examples of the storage medium MM include a flash memory, an optical disk, a memory card, and a hard disk. A part of or the entire predetermined computer program can be transferred from the storage medium MM to the memory 702 of the main controller 70 and stored. Conversely, a part of or the entire predetermined computer program can be transferred from the memory 702 of the main controller 70 to the storage medium MM and stored.

The irradiation control unit 71 is a computer that controls beam irradiation by the particle therapy system 1. Similarly to the main controller 70, the irradiation control unit 71, the CT control unit 72, and the operation terminal 74 include computer resources such as a microprocessor and a memory (none of them are illustrated).

The CT control unit 72 is a computer that controls the CT apparatus 5. Image data (diagnostic image data) of the target volume imaged by the CT apparatus 5 is stored in the data accumulation unit 73 via the CT control unit 72.

The data accumulation unit 73 stores, for example, the image data captured by the CT apparatus 5 and a treatment plan created by the treatment planning system 75.

The operation terminal 74 is a computer used by a user such as a doctor. The user operates the particle therapy system 1 by using the operation terminal 74. The user can acquire information from the particle therapy system 1 via the operation terminal 74 and confirm the information on a screen of the terminal 74.

The treatment planning system 75 is a computer that creates a plan for treating the patient Pt by beam irradiation. The treatment planning system 75 creates the treatment plan based on the image data obtained from the CT apparatus 5.

Figure 3:
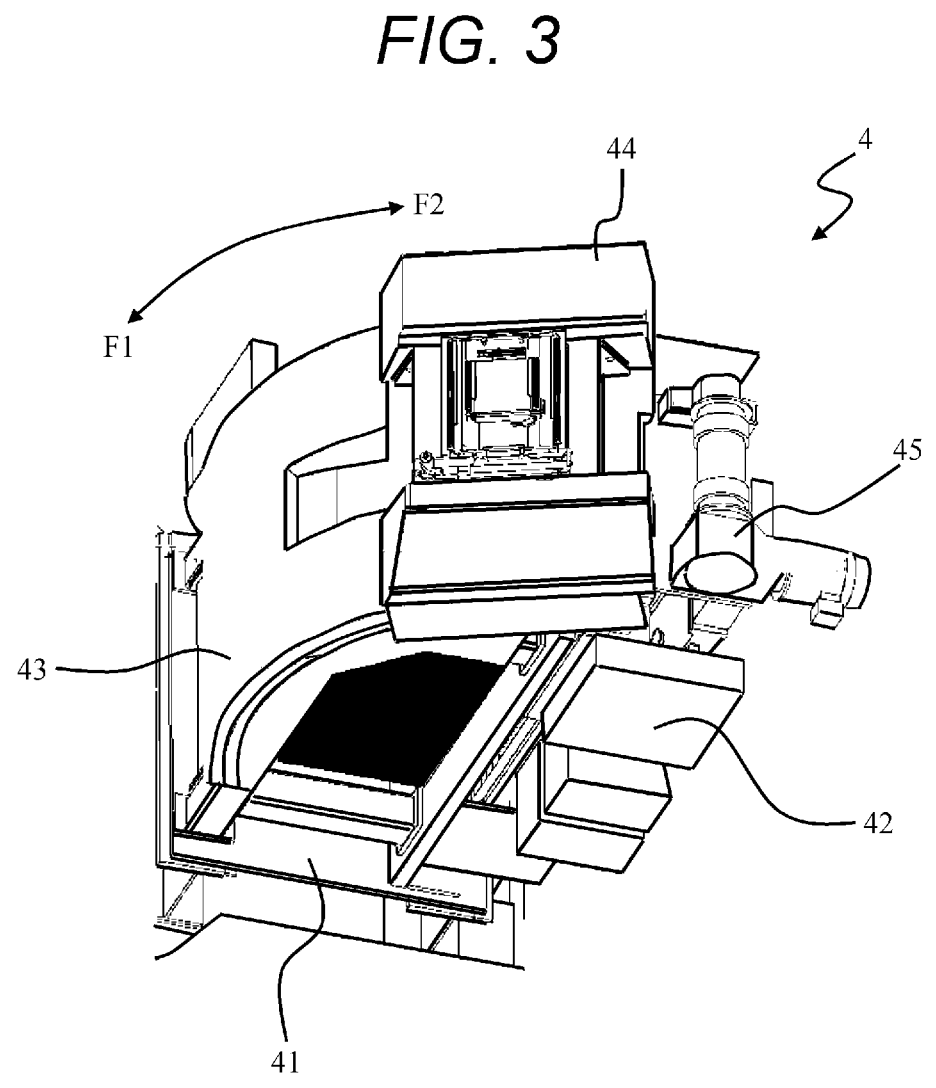
Figure 4:
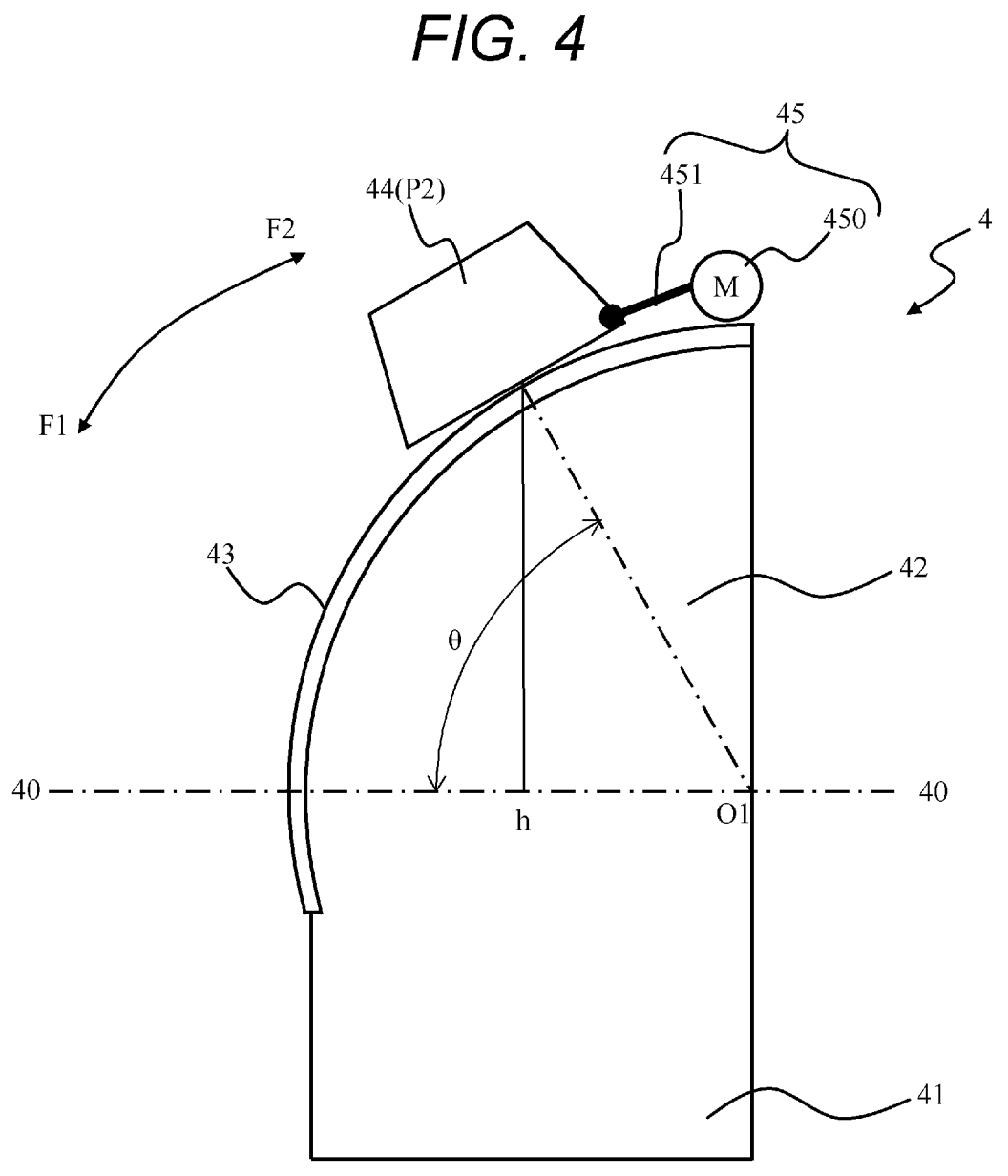
Figure 5:
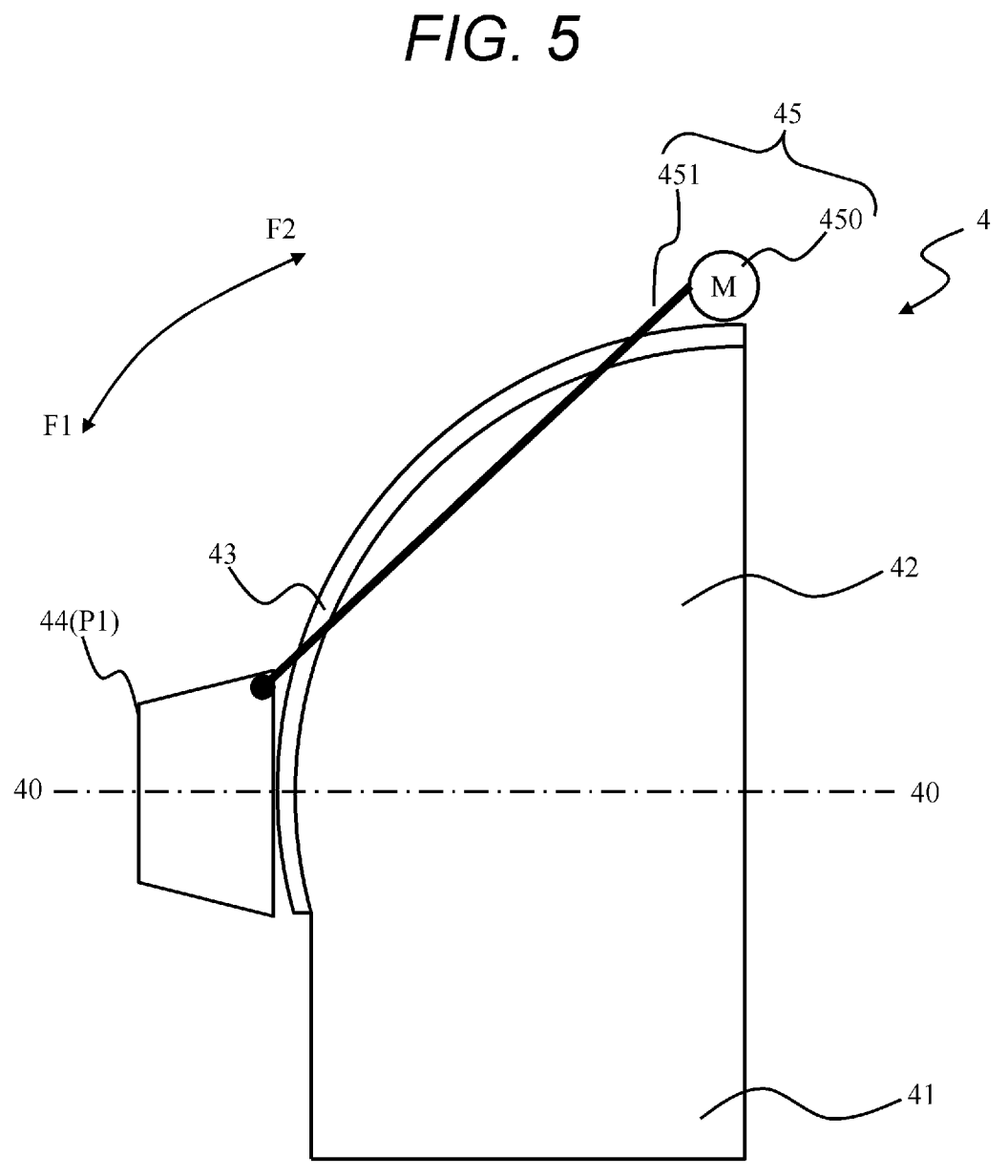

FIG. 3 is a perspective view of the irradiation nozzle 4 as viewed from above. FIG. 4 is a side view of the irradiation nozzle 4 when the nozzle tip part 44 is at the retraction position P2. FIG. 5 is a side view of the irradiation nozzle 4 when the nozzle tip part 44 is at the irradiation position P1.

The irradiation nozzle 4 includes, for example, a support part 41, the nozzle base part 42, the movement path 43, the nozzle tip part 44, and the nozzle drive unit 45.

The support part 41 is attached to the treatment room RM. The nozzle base part 42 is provided on an upper side of the support part 41, and includes a plurality of scanning magnets for deflecting and scanning a beam (none of them are illustrated).

The movement path 43 is provided on the downstream side of the nozzle base part 42 on the beam axis. The movement path 43 is formed in a curved or arc shape connecting the irradiation position P1 where the beam axis 40 passes through the nozzle base part 42 and the retraction position P2.

As illustrated in FIG. 4, the retraction position P2 is a position that deviates from the beam axis 40, is moved away from the irradiation position P1, and is separated from the patient Pt (in other words, the isocenter IC at the time of irradiation) by a predetermined distance. Specifically, the nozzle tip part 44 moves in the "predetermined direction" that is the direction F2 in which an intersection h between a perpendicular line drawn from the nozzle tip part 44 to the beam axis 40 and the beam axis 40 approaches the center point O1 positioned on a nozzle base part 42 side and set on the beam axis 40, on the arc-shaped movement path 43 connecting at least the irradiation position P1 and the retraction position P2 set above the center point O1 by the predetermined angle θ.

The nozzle tip part 44 is movably attached to the movement path 43 and moves in the directions of arrows F1 and F2 by the nozzle drive unit 45. The nozzle tip part 44 includes at least one device (not illustrated) such as a dose monitor, a position monitor, or a ridge filter.

The nozzle drive unit 45 includes, for example, a rotary motor 450 and a wire 451. The rotary motor 450 and a decelerator and a brake (none of them are illustrated) are provided on an upper side of the nozzle base part 42 and on a rear side (an upstream side in the beam flow direction) of the retraction position P2.

One of opposite ends of the wire 451 is connected to a rotation shaft of the rotary motor 450, and the other end is connected to the nozzle tip part 44. When the wire 451 is wound by the rotation of the rotary motor 450, the nozzle tip part 44 moves on the movement path 43 toward the retraction position P2 as illustrated in FIG. 4. When the wire 451 is unwound by reverse rotation of the rotary motor 450, the nozzle tip part 44 moves on the movement path 43 toward the irradiation position P1 as illustrated in FIG. 5.

Figure 6:
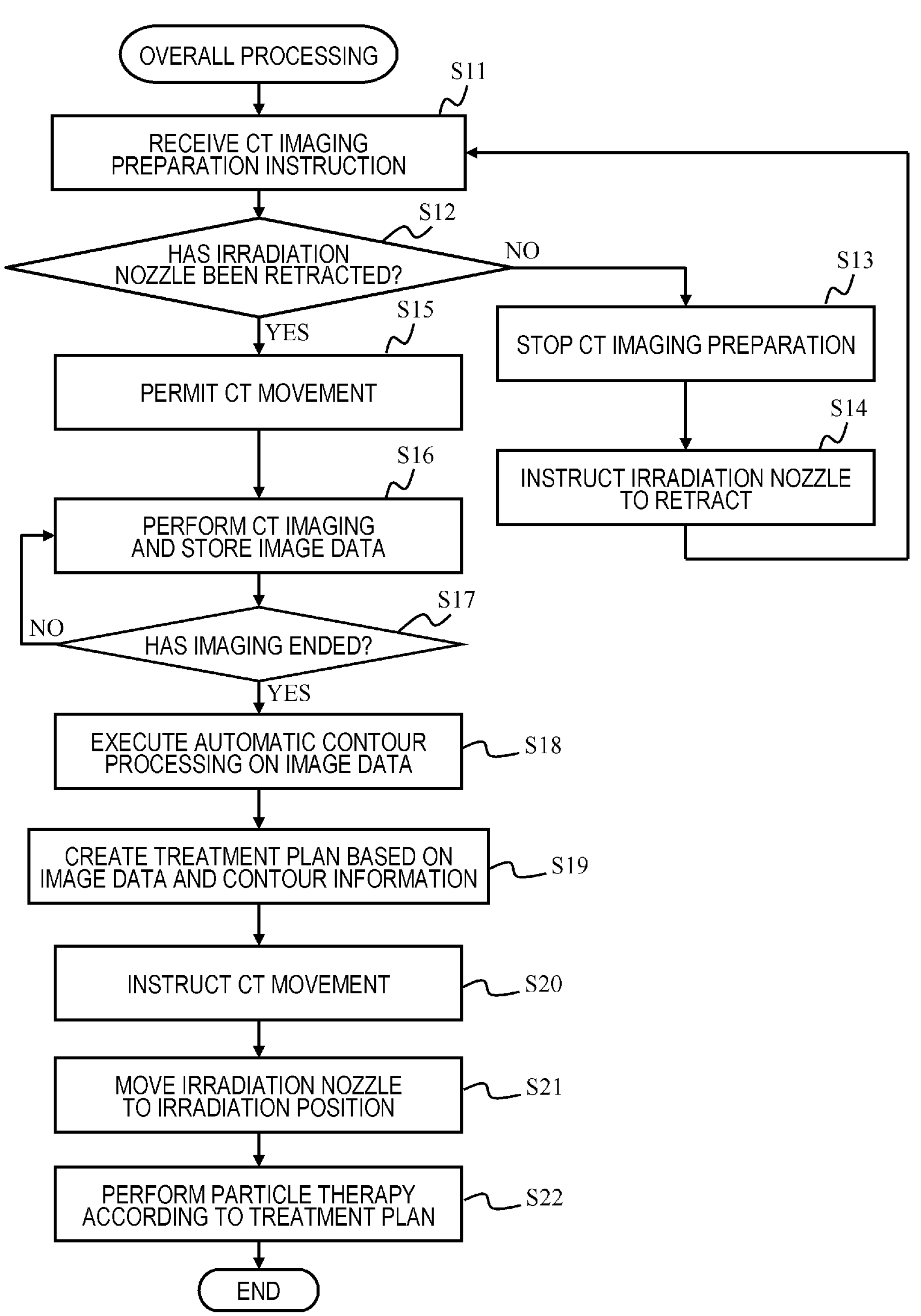
FIG. 6 is a flowchart illustrating overall processing in the particle therapy system.

The entire operation of the particle therapy system 1 in a case of an IGRT and adaptive therapy will be described with reference to the flowchart of FIG. 6.

When the start of preparation for imaging by the CT apparatus 5 is instructed from the operation terminal 74 (S11), the main controller 70 confirms the position of the irradiation nozzle 4 via the irradiation control unit 71, and determines whether or not the irradiation nozzle 4 has been retracted to the retraction position P2 (S12). In a case where it is determined that the irradiation nozzle 4 has not been retracted (S12: NO), the main controller 70 stops the preparation for imaging by the CT apparatus 5 (S13), and instructs the irradiation control unit 71 to retract the irradiation nozzle 4 (S14). As a result, the nozzle tip part 44 of the irradiation nozzle 4 moves on the movement path 43 in the direction of arrow F2 and is retracted to the retraction position P2.

When the user instructs the start of preparation for imaging by the CT apparatus 5 by using the operation terminal 74 again (S11), the main controller 70 determines that the nozzle tip part 44 has been retracted (S12: YES), and permits the CT apparatus 5 to move to the imaging position and perform imaging (S15). Since the nozzle tip part 44 of the irradiation nozzle 4 is retracted, the CT apparatus 5 and the irradiation nozzle 4 do not come into contact with each other even when the CT apparatus 5 moves from the standby place to the imaging position.

The CT apparatus 5 that has received the permission to move moves forward from the standby place on the back side of the drawing to the imaging position, images the patient Pt on the couch 6, and transmits the captured image data to the data accumulation unit 73 for storage (S16). Specifically, the CT apparatus 5 moves from a predetermined standby place to a treatment position (a position corresponding to the isocenter IC and a place where the target volume of the patient Pt can be imaged) in the irradiation room RM according to an instruction from the CT control unit 72.

The CT apparatus 5 passes the patient Pt through an opening 51 of the CT apparatus 5 from a distal end of the couch 6 according to an angle of the couch 6, moves to a place where the target volume can be imaged, and stands still. The CT apparatus 5 images the vicinity of the isocenter IC and transmits the image data to the CT control unit 72. The CT control unit 72 stores the image data received from the CT apparatus 5 in the data accumulation unit 73.

The main controller 70 confirms whether or not imaging by the CT apparatus 5 has ended via the CT control unit 72 (S17). In a case where it is confirmed that the imaging is completed (S17: YES), the main controller 70 executes automatic contour processing (segmentation processing) on the captured image data, and stores the contour information in the data accumulation unit 73 (S18).

The treatment planning system 75 creates a treatment plan based on the image data and the contour information stored in the data accumulation unit 73 (S19). The created treatment plan is transferred to and stored in the data accumulation unit 73. Instead of creating the treatment plan, a treatment plan created in advance may be corrected based on the image data. In addition, in a case where the creation of a treatment plan and the correction of a treatment plan are not performed, correction of a patient position based on the image data from the CT apparatus 5 is performed.

The main controller 70 instructs the CT apparatus 5 to return to the standby position according to a treatment start instruction input from the operation terminal 74 (S20). The main controller 70 instructs the nozzle tip part 44 of the irradiation nozzle 4 to move to the irradiation position P1 simultaneously with the instruction to move the CT apparatus 5 or after the instruction to move the CT apparatus 5 (S21). As a result, it is possible to smoothly transition from the CT imaging to the treatment by beam irradiation without moving the patient Pt.

When the nozzle tip part 44 of the irradiation nozzle 4 reaches the irradiation position P1, the irradiation control unit 71 causes the irradiation nozzle 4 to irradiate the target volume with a predetermined beam according to the treatment plan (S22).

Advantages of the configuration in which the nozzle tip part 44 is moved away in an arc shape (curved shape) while being deviated from the beam axis 40 will be described with reference to FIGS. 7 and 8.

Figure 7:
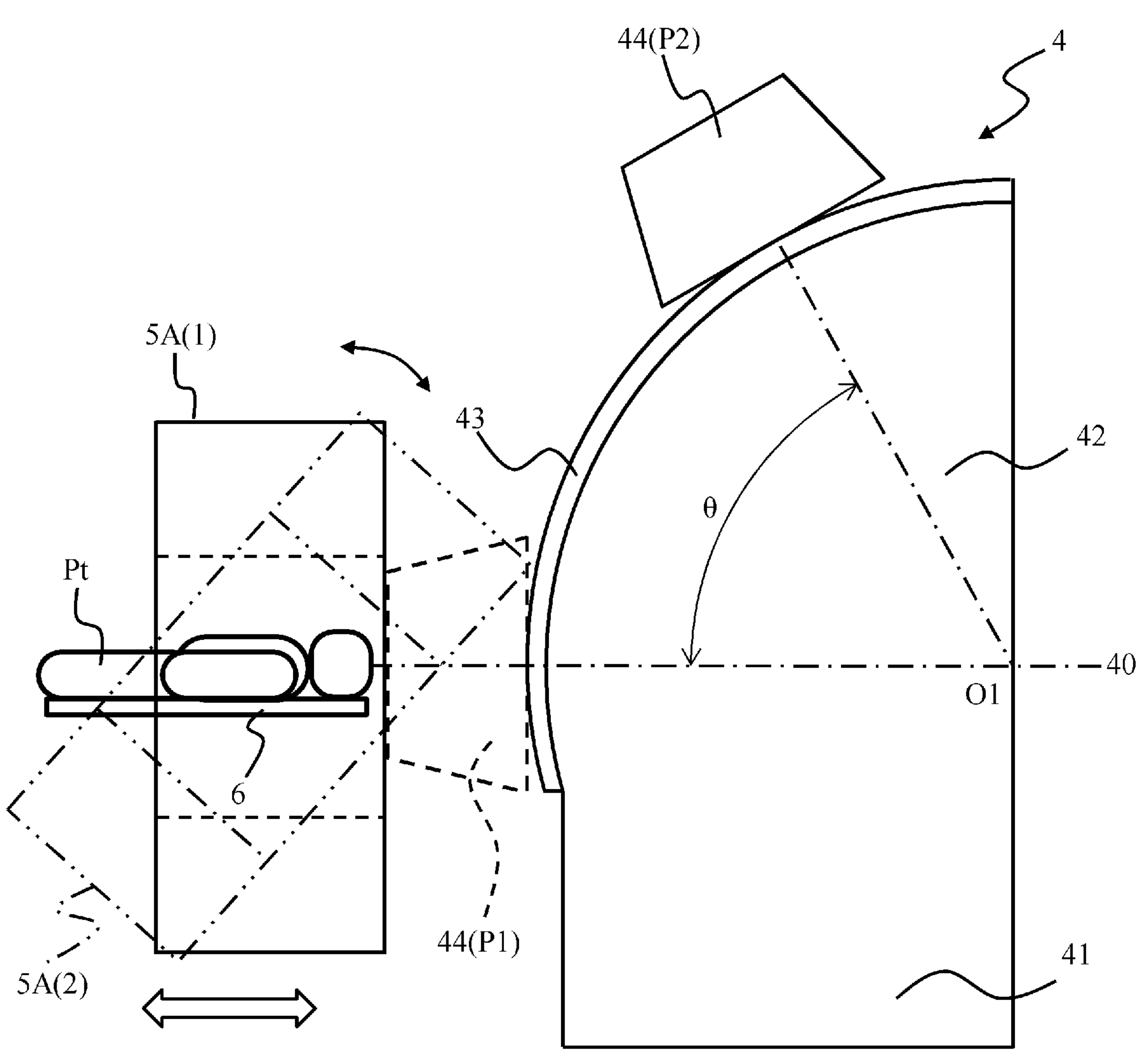
FIG. 7 is an explanatory view illustrating a relationship between a CT apparatus having a tilt function and the irradiation nozzle.

FIG. 7 illustrates a relationship between a CT apparatus 5A having a tilt function and the irradiation nozzle 4. In FIGS. 1 and 2, a case where a movement direction of the CT apparatus 5 and the beam axis 40 are orthogonal to each other has been described, but FIG. 7 illustrates a case where the movement direction of the CT apparatus 5A and the beam axis 40 coincide with each other.

The CT apparatus 5A of this modified example is movable in a left-right direction from a standby position (not illustrated) on the left side toward an imaging position illustrated in FIG. 7. Further, the CT apparatus 5A is tiltable from a vertical reference posture (5A (1)) to a tilted posture (5A (2)) at the imaging position. The CT apparatus 5A can also tilt counterclockwise from the vertical reference position (5A (1)).

In this manner, by retracting the nozzle tip part 44 from the irradiation position P1 to the retraction position P2 on the upper side of the nozzle base part 42 in such a way as to trace an arc-shaped trajectory, it is possible to cope with the tilt of the CT apparatus 5A.

Figure 8:
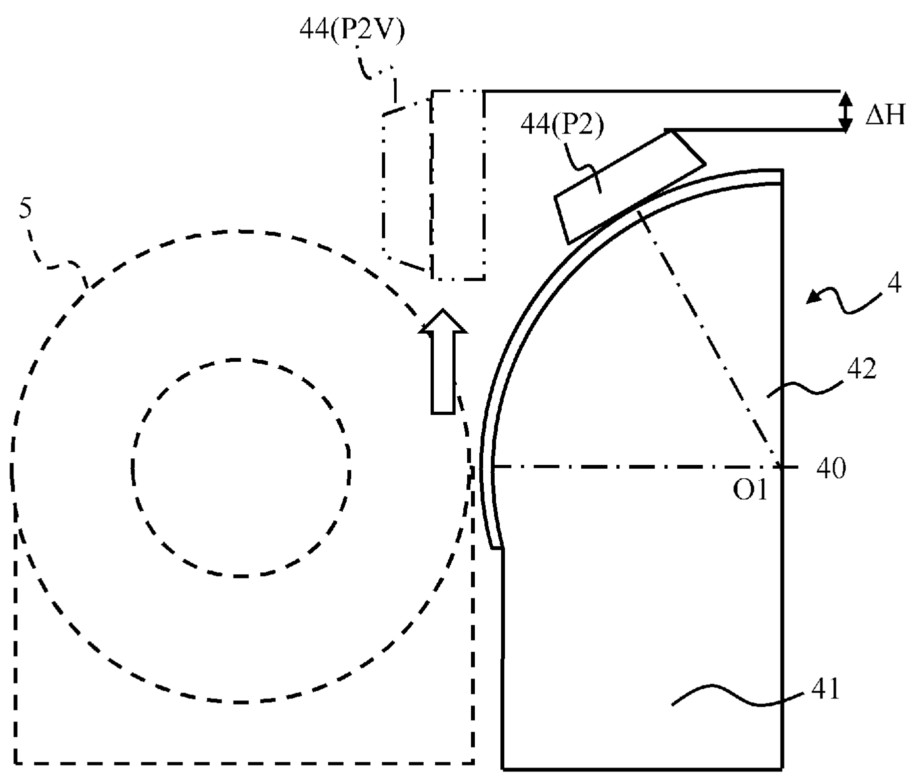
FIG. 8 is an explanatory view illustrating comparison with a case where the nozzle tip part moves perpendicular to a beam axis.

FIG. 8 illustrates comparison between a case where the nozzle tip part 44 moves perpendicular to the beam axis 40 and a case where the nozzle tip part 44 retracts while tracing an arc-shaped trajectory. An upper end position of the nozzle tip part 44 (P2V) that has moved perpendicularly is higher than an upper end position of the nozzle tip part 44 (P2) that has retracted while tracing the arc-shaped trajectory by a dimension ΔH.

Therefore, by retracting the nozzle tip part 44 to the retraction position P2 in such a way as to trace the arc-shaped trajectory, the height of the irradiation nozzle 4 can be reduced as compared with a case where the nozzle tip part 44 is retracted by moving perpendicularly.

According to the present embodiment, it is not necessary to move the patient Pt or change the posture between imaging by the CT apparatus 5 and beam irradiation by the irradiation nozzle 4, and thus, it is possible to suppress fluctuation of a body tissue accompanying the movement of the patient Pt or the like. Therefore, according to the present embodiment, since irradiation with the beam can be performed with highly accurate positioning, a margin for tissues around the target volume can be reduced, and a dose for a normal tissue can be reduced.

Furthermore, in the present embodiment, the nozzle tip part 44 of the irradiation nozzle 4 is moved away from the irradiation position P1 toward an upstream side on the beam axis 40 and moved in the direction F2 deviating from the beam axis 40 instead of being extended and contracted along the beam axis, so that the entire irradiation nozzle 4 can be downsized as compared with PTL 1.

Furthermore, in the present embodiment, it is also possible to cope with a tilt operation of the CT apparatus 5A. Furthermore, in the present embodiment, the isocenter of the irradiation beam and the isocenter of the imaging can be matched, and the treatment and the imaging can be performed without moving the treatment target on the top plate, so that the accuracy of the treatment can be improved. Therefore, in a case where, for example, a CT apparatus is introduced as the imaging apparatus, high-quality imaging can be performed, and the imaging apparatus can also be applied to the high-accuracy IGRT and adaptive treatment.

Second Embodiment

Figure 9:
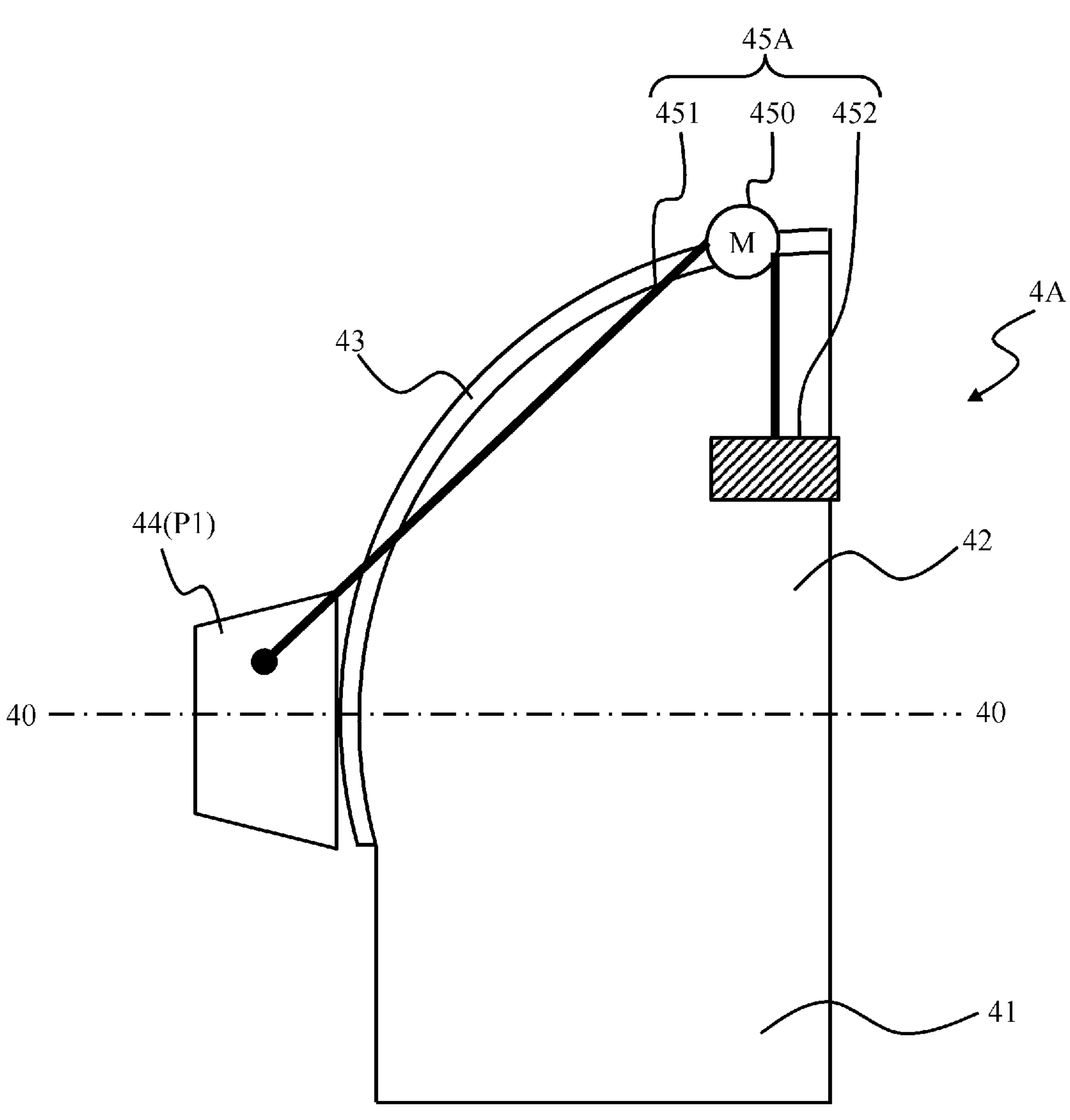
FIG. 9 is an explanatory view of an irradiation nozzle according to a second embodiment.

A second embodiment will be described with reference to FIGS. 9 and 10. In the present embodiment, differences from the first embodiment will be mainly described.

An irradiation nozzle 4A of the present embodiment uses a counterweight 452 to balance weights of opposite ends of a wire 451 and reduce a torque required for a rotary motor 450. That is, a nozzle drive unit 45A of the present embodiment includes the counterweight 452 in addition to the rotary motor 450 and the wire 451. The counterweight 452 is provided at one of the opposite ends of the wire 451 that is not connected to a nozzle tip part 44.

Figure 10:
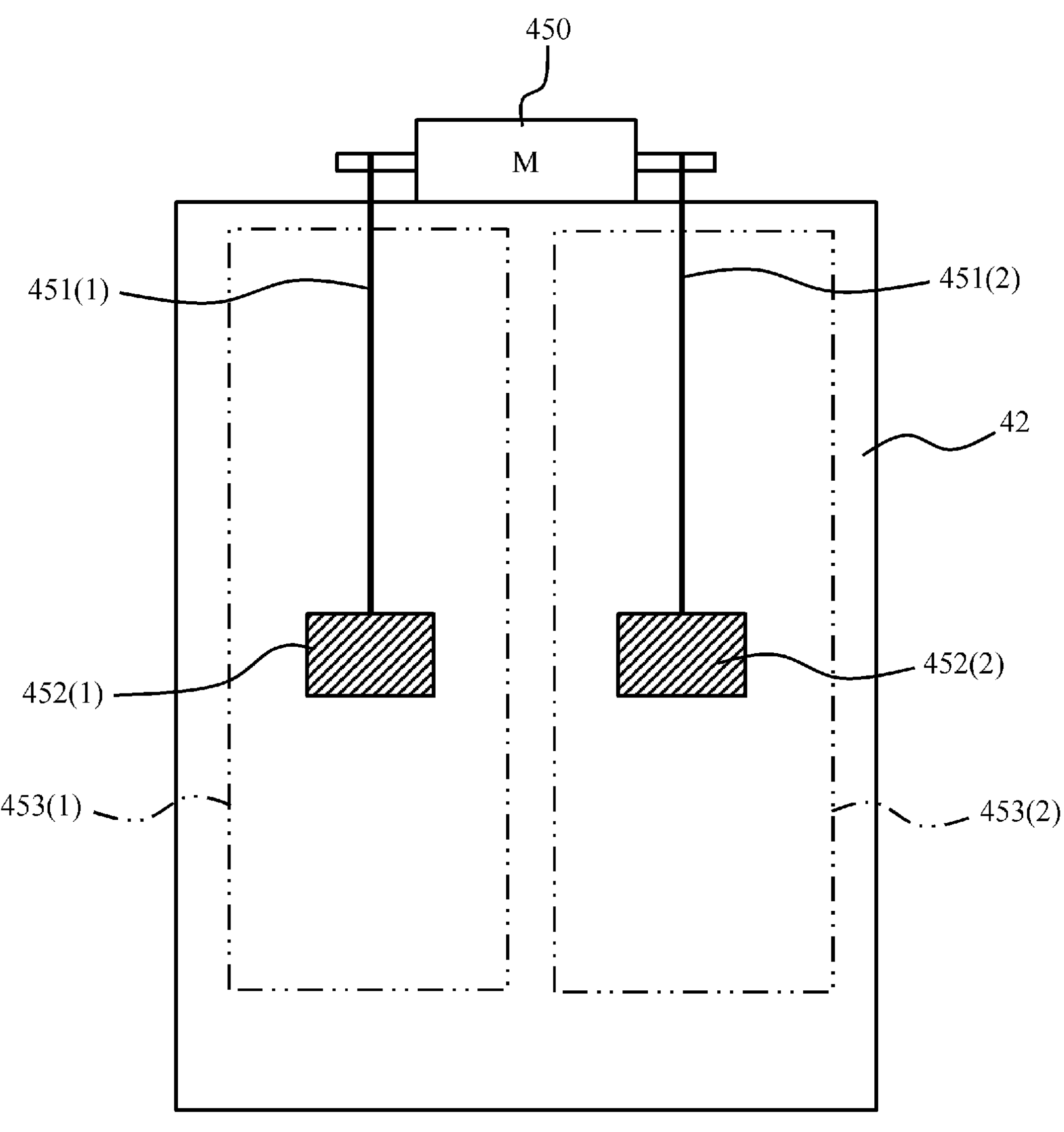
FIG. 10 is an explanatory view of the irradiation nozzle as viewed from behind.

FIG. 10 is an explanatory view of a nozzle base part 42 as viewed behind. Wires 451 (1) and 451 (2) may be wound around opposite ends of a rotation shaft of the rotary motor 450, respectively, one end of the opposite ends of each of the wires 451 (1) and 451 (2) may be connected to the nozzle tip part 44, and counterweights 452 (1) and 452 (2) may be provided at the other ends of the wires 451 (1) and 451 (2). Safety covers 453 (1) and 453 (2) may be provided to prevent the counterweights 452 (1) and 452 (2) moving up and down from coming into contact with an operator or the like.

The wire 451 and the counterweight 452 may be provided only at one end of the rotation shaft of the rotary motor 450.

The present embodiment configured as described above also has the same effects as the first embodiment. Furthermore, since the nozzle drive unit 45A of the present embodiment uses the counterweight 452, a load of the rotary motor 450 can be reduced, and the cost reduction and the long life of the rotary motor 450 can be implemented.

Figure 11:
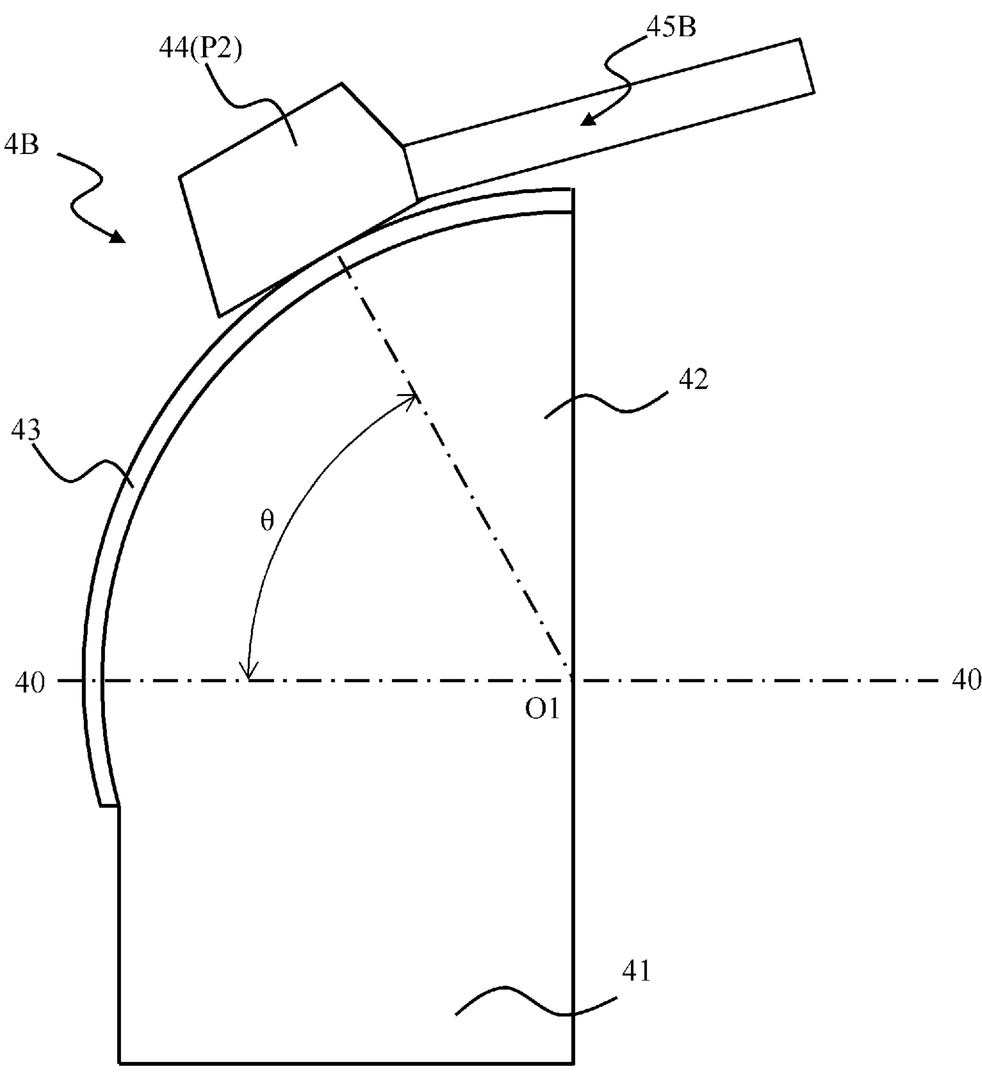
FIG. 11 is an explanatory view of an irradiation nozzle according to a modified example.

FIG. 11 is an explanatory view of an irradiation nozzle 4B according to a modified example. The irradiation nozzle 4B includes a nozzle drive unit 45B including a linear actuator. For example, a linear motor, a combination of an electric motor and a ball screw, a combination of an electric motor and a slider, a pneumatic cylinder, or the like can be used as the nozzle drive unit 45B.

Third Embodiment

Figure 12:
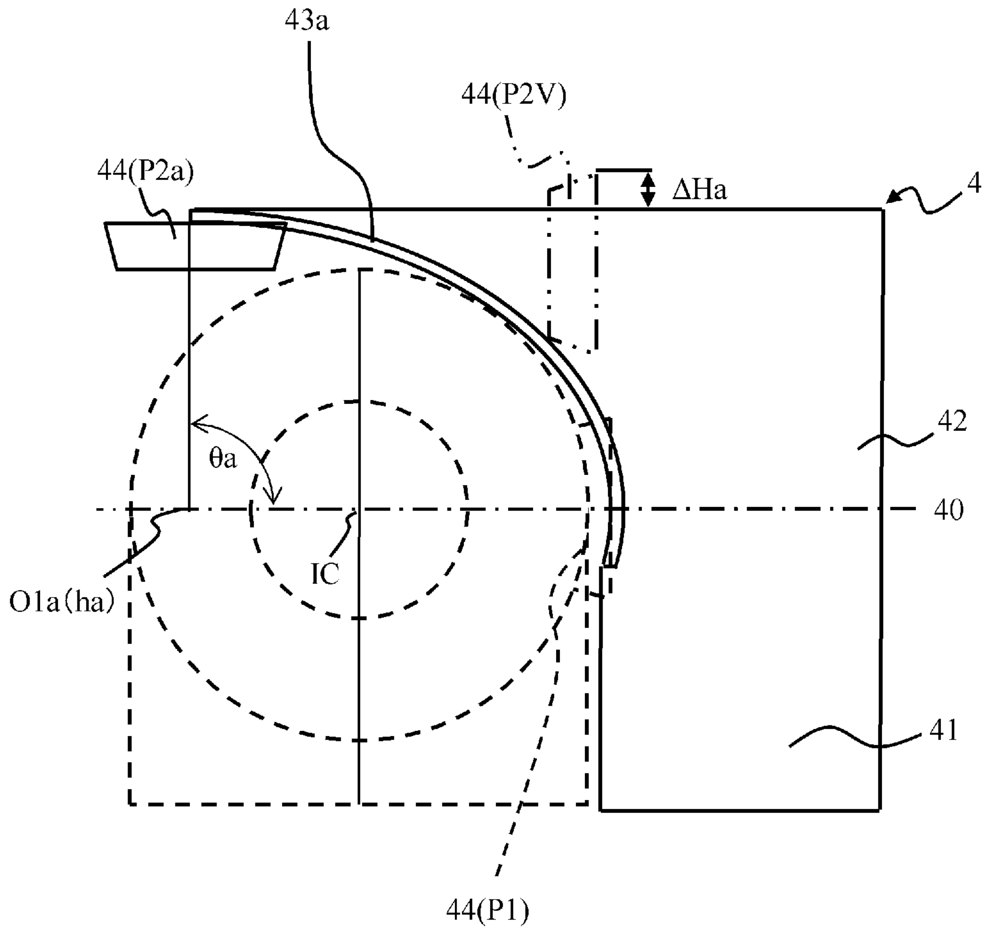
FIG. 12 is an explanatory view of an irradiation nozzle according to a third embodiment.

A third embodiment will be described with reference to FIG. 12. In the present embodiment, differences from the first embodiment and the second embodiment will be mainly described.

In the present embodiment, a center point 1*a* of a movement path 43 on an arc is positioned on a downstream side of a nozzle tip part 44 on a beam axis. For example, it is sufficient if the center point Ola is positioned on the beam axis and positioned on the downstream side of the nozzle tip part 44 on the beam axis, and the center point Ola is not necessarily limited to be positioned on the beam axis and may be positioned at a position deviated from the beam axis. As an example, as illustrated in FIG. 12, the center point Ola may coincide with an intersection ha between a perpendicular line drawn from the nozzle tip part 44 to a beam axis 40 and the beam axis 40 when the nozzle tip part 44 is at a retraction position P2*a*, or may coincide with an isocenter IC.

The nozzle tip part 44 moves in a "predetermined direction" that is a direction in which the intersection ha between the perpendicular line drawn from the nozzle tip part 44 to the beam axis 40 and the beam axis 40 approaches the downstream side on the beam axis, on the arc-shaped movement path 43*a* connecting at least an irradiation position P1 and the retraction position P2*a* set above the point O1*a* (center point O1*a*) by a predetermined angle θa, the point Ola being positioned downstream of the nozzle tip part 44 and being set on the beam axis 40.

As an example, the movement path 43*a* is formed in a curved shape connecting positions by rotating a predetermined angle of approximately 90 degrees counterclockwise from an intersection between the beam axis 40 and the downstream side (irradiation position P1) of the nozzle base part 42 on the beam axis around the point O1*a* set downstream of the nozzle tip part 44 on the beam axis 40. The curved movement path 43*a* can also be referred to as the arc-shaped movement path 43*a*. The arc shape is not limited to a part of a perfect circle, and may be a part of a circular shape other than the perfect circle. It is sufficient if the predetermined angle is an angle including an angle θa by which the nozzle tip part 44 moves between the irradiation position P1 and the retraction position P2*a*, and may be 90 degrees or more or less than 90 degrees.

According to the present embodiment, similarly to the first embodiment, by retracting the nozzle tip part 44 to the retraction position P2*a* in such a way as to trace the arc-shaped trajectory, the height of the irradiation nozzle 4 can be reduced by a height dimension ΔHa as compared with a case where the nozzle tip part 44 is retracted by moving perpendicularly as illustrated in FIG. 8.

Although the CT apparatus has been described as an example of the imaging apparatus, an outer shape of the CT apparatus is not necessarily a perfect circle. In addition, a non-annular imaging apparatus such as an open MRI can be used as the imaging apparatus. For example, in a case of using an imaging apparatus whose lateral width is larger than a height thereof, the nozzle tip part 44 is moved to the retraction position P2*a* above the imaging apparatus, whereby the patient Pt can be imaged at the isocenter IC position without interference between the nozzle tip part 44 and the imaging apparatus.

In the first embodiment, a case where one beam axis 40 horizontal to a floor surface is used has been described as an example, but the present embodiment can also be applied to an irradiation nozzle that performs beam irradiation in a plurality of directions. That is, the irradiation nozzle 4 can be applied not only to an irradiation nozzle whose beam axis is horizontal to the floor surface but also to an irradiation nozzle that can perform beam irradiation in a plurality of different directions such as a case where a beam axis forms 45° with the floor surface or a case where the beam axis is perpendicular to the floor surface. The present invention can also be applied to a particle therapy system in which the nozzle base part 42 includes a bending magnet that continuously changes an irradiation angle, and the nozzle tip part 44 is moved to perform beam irradiation from an arbitrary angle. At this time, a scanning magnet may be provided at the nozzle tip part 44 instead of the nozzle base part 42, or may be provided on the upstream side of the nozzle base part 42 on the beam.

Note that the present invention is not limited to the above-described embodiments. Those skilled in the art can make various additions, modifications, and the like without departing from the scope of the present invention. The above-described embodiments are not limited to the configuration example illustrated in the accompanying drawings. The configurations and the processing methods of the embodiments can be appropriately changed within the scope of achieving the object of the present invention.

REFERENCE SIGNS LIST

1 particle therapy system
2 particle generator
3 beam transport system
4, 4A, 4B irradiation nozzle
5, 5A CT apparatus
6 couch
7 control system
10 particle therapy apparatus
41 support part
42 nozzle base part
43 movement path
44 nozzle tip part
45, 45A, 45B nozzle drive unit

The invention claimed is:

1. An irradiation nozzle that irradiates a target object with a radiotherapy beam, the irradiation nozzle comprising:
- a nozzle base part fixed on a beam axis through which the radiotherapy beam passes;
- a nozzle tip part that irradiates the target object with the radiotherapy beam that has passed through the nozzle base part, wherein
- the nozzle tip part is fixed at a first position when the target object is irradiated with the radiotherapy beam and is fixed at a second position when the target object is imaged,
- a curved movement path is position on a downstream side of the nozzle base part in which the nozzle tip part is movable between the first position and the second position relative to the beam axis, and
- the first position and the second position are different positions on the curved movement path.

2. The irradiation nozzle according to claim 1, wherein the beam axis is horizontal to a floor surface.

3. The irradiation nozzle according to claim 1, wherein the second position deviates from the beam axis.

4. The irradiation nozzle according to claim 1, wherein
- the curved movement path has a substantially arc shape, and
- a center of an arc drawn by the movement path is positioned upstream of the nozzle tip part.

5. The irradiation nozzle according to claim 1, wherein
- the curved movement path has a substantially arc shape, and
- a center of an arc drawn by the movement path is positioned downstream of the nozzle tip part.

6. The irradiation nozzle according to claim 1, wherein
- the nozzle tip part is stoppable at an arbitrary position on the movement path.

7. The irradiation nozzle according to claim 1, wherein
- the predetermined movement path is formed in a curved shape according to a tilt angle of a tiltable apparatus disposed in front of the nozzle base side while being spaced apart from the nozzle base side along the beam axis.

8. The irradiation nozzle according to claim 1, wherein
- the nozzle tip part is moved by a nozzle drive unit, and
- the drive unit includes a rotary motor that winds or unwinds a wire.

9. The irradiation nozzle according to claim 1, wherein
- the radiotherapy beam is a particle beam, and
- the nozzle tip part includes at least one of a dose monitor, a position monitor, or a ridge filter.

10. The irradiation nozzle according to claim 1, wherein
- the radiotherapy beam is a particle beam, and
- the nozzle base part includes a scanning magnet.

11. A particle therapy apparatus comprising:
- the irradiation nozzle according to claim 1; and
- an accelerator that accelerates the radiotherapy beam.

12. A particle therapy system comprising:
- the particle therapy apparatus according to claim 11; and
- an imaging apparatus that images an inside of the target object, wherein
- the imaging apparatus is movable between an imaging position at which the target object on the beam axis is imaged and a standby position at which the imaging apparatus does not interfere with the nozzle tip part when the nozzle tip part is at the first position.

13. The particle therapy system according to claim 12, further comprising a control apparatus, wherein
- when it is detected that imaging by the imaging apparatus is completed, the control apparatus starts segmentation by using a captured image.

14. The particle therapy system according to claim 13, wherein when it is detected that the segmentation by the particle therapy system is completed, the control apparatus further starts treatment plan creation by using segmented contour information.

15. A method for controlling a particle therapy system, wherein the particle therapy system includes a particle therapy apparatus, an imaging apparatus for a target object, and a control apparatus, the particle therapy apparatus includes an accelerator that accelerates a radiotherapy beam, and an irradiation nozzle that irradiates the target object with the accelerated radiotherapy beam, the irradiation nozzle includes a nozzle base part fixed on a beam axis through which the radiotherapy beam passes, and a nozzle tip part that irradiates the target object with the radiotherapy beam having passed through the nozzle base part, the nozzle tip part is fixed at a first position when the target object is irradiated with the radiotherapy beam and is fixed at a second position when the target object is imaged, a curved movement path is positioned on a downstream side of the nozzle base part through which the nozzle tip part is movable between the first position and the second position relative to the beam axis, and the first and the second position are different positions on the curved movement path, and the imaging apparatus is movable between an imaging position at which the target object on the beam axis is imaged and a standby position at which the imaging apparatus does not interfere with the nozzle tip part when the nozzle tip part is at the irradiation position.

16. A method for controlling a particle therapy system, wherein the particle therapy system includes a particle therapy apparatus, an imaging apparatus for a target object, and a control apparatus, the particle therapy apparatus includes an accelerator that accelerates a radiotherapy beam, and an irradiation nozzle that irradiates the target object with the accelerated radiotherapy beam, the irradiation nozzle includes a nozzle base part fixed on a beam axis through which the radiotherapy beam passes, and a nozzle tip part that irradiates the target object with the radiotherapy beam having passed through the nozzle base part, the nozzle tip part is fixed at a first position when the target object is irradiated with the radiotherapy beam and is fixed at a second position when the target object is imaged, a curved movement path is positioned on a downstream side of the nozzle base part through which the nozzle tip part is movable between the first position and the second position relative to the beam axis, and the first position and the second position are different positions on the curved movement path, the imaging apparatus is movable between an imaging position at which the target object on the beam axis is imaged and a standby position at which the imaging apparatus does not interfere with the nozzle tip part when the nozzle tip part is at the irradiation position, and when it is detected that imaging by the imaging apparatus is completed, the control apparatus starts segmentation by using a captured image.

17. A method for controlling a particle therapy system, wherein the particle therapy system includes a particle therapy apparatus, an imaging apparatus for a target object, and a control apparatus, the particle therapy apparatus includes an accelerator that accelerates a radiotherapy beam, and an irradiation nozzle that irradiates the target object with the accelerated radiotherapy beam, the irradiation nozzle includes a nozzle base part fixed on a beam axis through which the radiotherapy beam passes, and a nozzle tip part that irradiates the target object with the radiotherapy beam having passed through the nozzle base part, the nozzle tip part is fixed at a first position when the target object is irradiated with the radiotherapy beam and is fixed at a second position when the target object is imaged, a curved movement path is positioned on a downstream side of the nozzle base part through which the nozzle tip part is movable between the first position and the second position relative to the beam axis, and the first position and the second position are different positions on the curved movement path, the imaging apparatus is movable between an imaging position at which the target object on the beam axis is imaged and a standby position at which the imaging apparatus does not interfere with the nozzle tip part when the nozzle tip part is at the irradiation position, when it is detected that imaging by the imaging apparatus is completed, the control apparatus starts segmentation by using a captured image, and when it is detected that the segmentation by the particle therapy system is completed, the control apparatus further starts treatment plan creation by using segmented contour information.

* * * * *